United States Patent [19]

Bentley et al.

[11] 4,385,070
[45] May 24, 1983

[54] HALOGENATED ESTERS

[75] Inventors: Philip D. Bentley, Bracknell; Nazim Punja, Crowthorne, both of England

[73] Assignee: Imperial Chemical Industries Limited, London, England

[21] Appl. No.: 116,597

[22] Filed: Jan. 28, 1980

[30] Foreign Application Priority Data

Jan. 18, 1980 [EP] European Pat. Off. ............ 80300169
Feb. 14, 1979 [GB] United Kingdom ................. 7905239
Jan. 18, 1980 [GB] United Kingdom ................. 8001693

[51] Int. Cl.³ ..................... C07C 69/743; A01N 53/00
[52] U.S. Cl. ................................ 424/305; 260/465 B;
260/465 G; 260/465 D; 560/65; 560/66;
560/103; 560/124; 564/142; 564/161; 568/308;
568/312; 568/319; 568/812; 570/127; 424/304;
424/308
[58] Field of Search ................... 560/124, 65, 66;
260/465 D; 424/304, 305, 308

[56] References Cited

U.S. PATENT DOCUMENTS

| | | | |
|---|---|---|---|
| 3,673,215 | 6/1972 | Vollrath | 560/124 |
| 3,792,079 | 2/1974 | D'Orazio | 560/124 |
| 4,024,163 | 5/1977 | Elliott | 560/124 |
| 4,183,948 | 1/1980 | Huff | 424/304 |
| 4,183,950 | 1/1980 | Naumann | 560/124 |
| 4,243,677 | 1/1981 | Engel | 560/124 |
| 4,252,820 | 2/1981 | Lantzsch | 560/124 |

FOREIGN PATENT DOCUMENTS 862109 6/1978 Belgium .
2379506 9/1978 France .
40-11499 6/1965 Japan .................................. 560/124

OTHER PUBLICATIONS

Elliott, Chem. Soc. Rev., 7, pp. 473–505 (1978).

Primary Examiner—Michael L. Shippen
Attorney, Agent, or Firm—Cushman, Darby & Cushman

[57] ABSTRACT

Compounds of formula I wherein $R^1$ and $R^2$ are each selected from halomethyl and halo and R is nitro, cyano, lower alkoxycarbonyl, lower alkylcarbonyl, or di- or trifluoromethyl, and n has a value of zero to four, and compositions comprising them are useful as insecticides in agriculture, horticulture and other outlets. They may optionally be combined with other pesticides and/or synergists. The compounds may be prepared by conventional esterification processes from the corresponding acids and appropriately substituted benzyl alcohols or halides, some of which are novel.

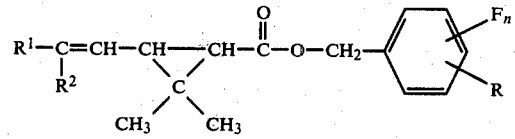

2 Claims, No Drawings

HALOGENATED ESTERS

This invention relates to novel cyclopropane derivatives useful as insecticides, to processes for their preparation, to compositions comprising them and to methods of combatting insect and similar invertebrate pests using them.

Certain naturally occurring esters of cyclopropane carboxylic acids have long been known to possess insecticidal properties, but these compounds have been too easily degraded by ultra violet light to be of much use in agriculture. Several groups of synthetic compounds based on cyclopropane carboxylic acids (for example those disclosed in British patent specifications Nos. 1,243,858 and 1,413,491) have been evaluated in an attempt to discover compounds of sufficient light stability for use as general agricultural insecticides.

A particularly useful group of such compounds is that disclosed in British patent specification No. 2,000,764 and Belgian Pat. No. 863,151. These compounds combine good light stability with excellent contact and residual insecticidal properties, but, in common with the compounds described in British patent specification Nos. 1,243,858 and 1,413,491, they possess little or no fumigant activity. A further group of compounds, halobenzyl esters of 3-(2,2-dihalovinyl)-2,2-dimethylcyclopropane carboxylic acids, is described in Belgian Pat. No. 862,109 as having insecticidal properties but there is no indication that the compounds possess fumigant activity.

The present invention relates to certain novel benzyl esters of 3-(2,2-dihalovinyl)-2,2-dimethylcyclopropane carboxylic acids and 3-(2-halo(or trifluoromethyl)-3,3,3-trifluoropropenyl)-2,2-dimethylcyclopropane carboxylic acids with an extremely high level of insecticidal and acaricidal activity which may be used not only as contact or residual insecticides but also as fumigant insecticides.

Accordingly this invention provides compounds of formula:

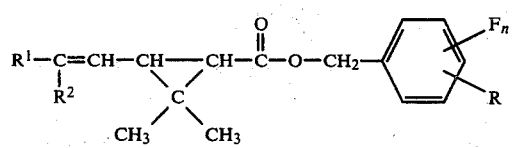

wherein $R^1$ and $R^2$ are each selected from halomethyl and halo; R is nitro, cyano, lower alkoxycarbonyl, lower alkylcarbonyl, or di- or trifluoromethyl, and n has a value from zero to four. The term "lower alkoxycarbonyl" and "lower alkylcarbonyl" is used to indicate such groups containing up to four carbon atoms in the alkyl moiety.

In a preferred aspect the invention provides compounds of formula:

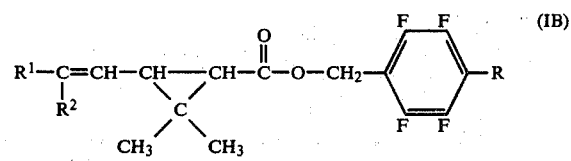

wherein $R^1$ and $R^2$ are both chloro, or one of $R^1$ and $R^2$ is chloro and the other is trifluoromethyl, and R is cyano, acetyl, methoxycarbonyl or trifluoromethyl.

Particular compounds according to the invention include those set out in Table I below. They conform to formula IC below and the meanings for $R^1$, $R^2$, $R^3$, $R^4$, $R^5$, $R^6$ and $R^7$ are given for each compound.

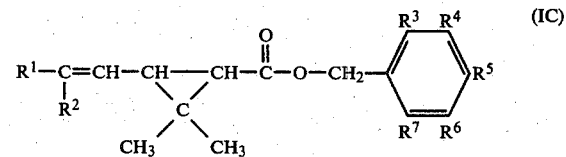

Of the compounds listed in Table I compounds 4 and 6 are especially useful insecticides having a broad spectrum of activity at extremely low rates of application.

TABLE I

| Compound No. | $R^1$ | $R^2$ | $R^3$ | $R^4$ | $R^5$ | $R^6$ | $R^7$ |
|---|---|---|---|---|---|---|---|
| 1 | $CF_3$ | Cl | $CF_3$ | H | H | H | H |
| 2 | $CF_3$ | Cl | H | $CF_3$ | H | H | H |
| 3 | $CF_3$ | Cl | $NO_2$ | H | F | H | H |
| 4 | $CF_3$ | Cl | F | F | $CF_3$ | F | F |
| 5 | $CF_3$ | Cl | H | F | $NO_2$ | H | H |
| 6 | Cl | Cl | F | F | $CF_3$ | F | F |
| 7 | $CF_3$ | Cl | F | H | H | $NO_2$ | H |
| 8 | $CF_3$ | Cl | F | F | $CO_2CH_3$ | F | F |
| 9 | $CF_3$ | Cl | F | F | $COCH_3$ | F | F |
| 10 | $CF_3$ | Cl | F | F | CN | F | F |
| 11 | $CF_3$ | Cl | H | H | $CF_3$ | H | H |

It will be appreciated by those skilled in the art that the compounds represented by formula I are capable of existing in various geometrical and stereoisomeric forms. Thus there may be cis and trans isomers arising from the substitution pattern of the cyclopropane ring, and E- and Z-isomers arising from the substituted vinyl group when $R^1$ is not identical with $R^2$. In addition two of the three carbon atoms of the cyclopropane are capable of existing in either R- or S-configurations since they are asymmetrically substituted. Within the group of compounds represented by Formula I the cis isomers usually have better insecticidal properties than the trans isomers or the mixture of cis and trans isomers; the (+)-cis isomers being particularly preferred.

A particularly useful single isomer of a compound according to the invention is the 4-trifluoromethyltetrafluorobenzyl ester of (+)-cis-3-(Z-2-chloro-3,3,3-trichloroprop-1-en-yl)-2,2-dimethylcyclopropane carboxylic acid, which is believed to have the (1R,3R) configuration in the cyclopropane ring.

The compounds of the invention according to Formula I are esters and may be prepared by conventional esterification processes, of which the following are examples.

(a) An acid of formula:

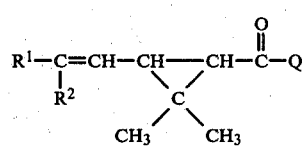

where Q represents the hydroxy group and $R^1$ and $R^2$ have any of the meanings given hereinabove, may be reacted directly with an alcohol of formula:

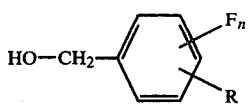

(III)

where n and R have any of the meanings given hereinabove, the reaction preferably taking place in the presence of an acid catalyst, for example, dry hydrogen chloride.

(b) An acid halide of formula II where Q represents a halogen atom, preferably a chlorine atom, and $R^1$ and $R^2$ have any of the meanings given hereinabove, may be reacted with an alcohol of formula III, the reaction preferably taking place in the presence or a base, for example, pyridine, alkali metal hydroxide or carbonate, or alkali metal alkoxide.

(c) An acid of formula II or, preferably, an alkali metal salt thereof, may be reacted with halide of formula:

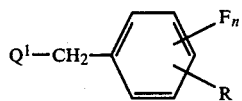

(IV)

where $Q^1$ represents a halogen atom, preferably the bromine or chlorine atom, and n and R have any of the meanings given hereinabove, or with the quaternary ammonium salts derived from such halides with tertiary amines, for example pyridine, or trialkyl amines such as triethylamine.

(d) A lower alkyl ester of formula (II) where Q represents a lower alkoxy group containing up to six carbon atoms, preferably the methoxy or ethoxy group, and $R^1$ and $R^2$ have any of the meanings given hereinabove, is heated with an alcohol of formula III to effect a transesterification reaction. Preferably the process is performed in the presence of a suitable catalyst, for example, an alkali metal alkoxide, such as sodium methoxide, or an alkylated titanium derivative, such as tetramethyl titanate.

All of these conventional processes for the preparation of esters may be carried out using solvents and diluents for the various reactants where appropriate, and may be accelerated or lead to higher yields of product when performed at elevated temperatures or in the presence of appropriate catalysts, for example phase-transfer catalysts.

The preparation of individual isomers may be carried out in the same manner but commencing from the corresponding individual isomers of compounds of formula II. These may be obtained by conventional isomer separation techniques from mixtures of isomers. Thus cis and trans isomers may be separated by fractional crystallisation of the carboxylic acids or salts thereof, whilst the various optically active species may be obtained by fractional crystallisation of salts of the acids with optically active amines, followed by regeneration of the optically pure acid.

The optically pure isomeric form of the acid (or its equivalent acid chloride or ester) may then be reacted with the appropriate alcohol to produce a compound of formula I in the form of an individually pure isomer thereof.

The preparation of the compounds of formula II wherein Q is hydroxy, alkoxy or halo, and $R^1$ and $R^2$ are as defined hereinabove, useful as intermediates in the preparation of the compounds of the invention, is fully described in British Patent Specification No. 2,000,764 and in Belgian Pat. No. 863151, or British Patent Specification No. 1,413,491.

Some of the compounds of formulae III and IV are believed not to have been described before. In a further aspect therefore the invention provides compounds of formulae

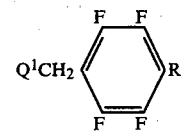

(V)

wherein R is cyano, trifluoromethyl, lower alkoxycarbonyl or lower alkylcarbonyl, and $Q^1$ is hydroxy, chloro or bromo.

The compounds of formula IV and V may be prepared by chlorinating or bromination of the corresponding methyl derivatives by bringing the latter into contact with a source of positive chlorine or bromine, such as an N-chloro- or N-bromoimide for example N-chlorosuccinimide or N-bromosuccinimide. Some of the methyl derivatives are known, but those of formula VI

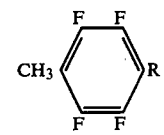

where R is cyano, alkylcarbonyl or alkoxycarbonyl have not previously been described. They may be prepared by carboxylation of the corresponding methyltetrafluorobenzene (for example by the use of an organometallic reagent such as an alkyl lithium followed by decomposition of the reaction product with carbon dioxide) and subsequent derivativisation of the carboxylic acid group, as set out in Scheme A.

SCHEME A

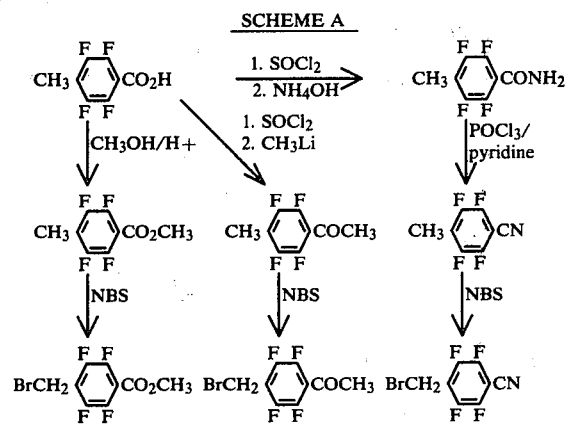

SCHEME B

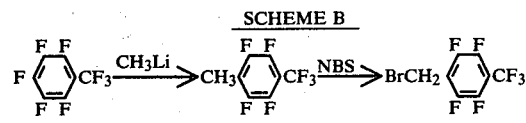

Similarly the compound of formula (V) where R is trifluoromethyl may be prepared by methylation of octafluorotoluene, and converted to the bromo derivative by N-bromosuccinimide treatment as shown in Scheme B. The alcohols of formula

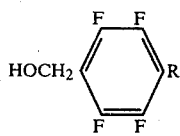

may be obtained by partial reduction of the corresponding carboxylic acids.

When the processes for preparing the compounds of Formula I are performed using intermediates which are themselves mixtures of isomers the products obtained will also be mixtures of isomers. Thus, the product would be a mixture of (±)-cis and (±)-trans isomers (perhaps with one form predominating) if the intermediate acid or acid derivatives was used in the form of a mixture of (±)-cis and (±)-trans isomers. If a single isomer, of the acid, e.g. the (+)-cis isomer with Z-configuration in the 2-chloro-3,3,3-trifluoropropenyl group, was used, the product would also be the single isomer of that stereochemical configuration, or a pair of isomers if there is an asymmetric carbon atom in the alcohol moiety.

In order to avoid confusion the products obtained by the processes described in the Examples herein are referred to as Products A to L, each product being defined in terms of isomeric composition with reference to the compounds of Table I as follows:

Product A: 2-trifluoromethylbenzyl 3-(2-chloro-3,3,3-trifluoroprop-1-en-1-yl)-2,2-dimethylcyclopropane carboxylate (compound No. 1, Table I) consisting of 50% w/w of the (±)-cis isomer and 50% w/w of the (±)-trans isomer.

Product B: 3-trifluoromethylbenzyl 3-(2-chloro-3,3,3-trifluoroprop-1-en-1-yl)-2,2-dimethylcyclopropane carboxylate (compound No. 2, Table I) consisting of 50% w/w of the (±)-cis isomer and 50% w/w of the (±)-trans isomer.

Product C: 2-nitro-4-fluorobenzyl 3-(2-chloro-3,3,3-trifluoroprop-1-en-1-yl)-2,2-dimethylcyclopropane carboxylate (compound No. 3, Table I) consisting of 50% w/w of the (±)-cis isomer and 50% w/w of the (±)-trans isomer.

Product D: 4-trifluoromethyltetrafluorobenzyl 3-(2-chloro-3,3,3-trifluoroprop-1-en-1-yl)-2,2-dimethylcyclopropane carboxylate (compound No. 4, Table I) consisting of 50% w/w of the (±)-cis isomer and 50% w/w of the (±)-trans isomer.

Product E: 3-fluoro-4-nitrobenzyl 3-(2-chloro-3,3,3-trifluoroprop-1-en-1-yl)-2,2-dimethylcyclopropane carboxylate (compound No. 5, Table I) consisting of 50% w/w of the (±)-cis isomer and 50% w/w of the (±)-trans isomer.

Product F: 4-trifluoromethyltetrafluorobenzyl 3-(2,2-dichlorovinyl)-2,2-dimethylcyclopropane carboxylate (compound No. 6, Table I) consisting of 50% w/w of the (±)-cis isomer and 50% w/w of the (±)-trans isomer.

Product G: 2-fluoro-5-nitrobenzyl 3-(2-chloro-3,3,3-trifluoroprop-1-en-1-yl)-2,2-dimethylcyclopropane carboxylate (compound No. 7, Table I) consisting of 50% w/w of the (±)-cis isomer and 50% w/w of the (±)-trans isomer.

Product H: 4-methoxycarbonyltetrafluorobenzyl 3-(2-chloro-3,3,3-trifluoroprop-1-en-1-yl)-2,2-dimethylcyclopropane carboxylate (compound No. 8, Table I) consisting of 50% w/w of the (±)-cis isomer and 50% w/w of the (±)-trans isomer.

Product J: 4-methylcarbonyltetrafluorobenzyl 3-(2-chloro-3,3,3-trifluoroprop-1-en-1-yl)-2,2-dimethylcyclopropane carboxylate consisting of 50% of the (±)-cis isomer and 50% w/w of the (±)-trans isomer.

Product K: 4-cyanotetrafluorobenzyl 3-(2-chloro-3,3,3-trifluoroprop-1-en-1-yl)-2,2-dimethylcyclopropane carboxylate (compound No. 10, Table I) consisting of 50% w/w of the (±)-cis isomer and 50% w/w of the (±)-trans isomer.

Product L: 4-trifluoromethylbenzyl 3-(2-chloro-3,3,3-trifluoroprop-1-en-1-yl)-2,2-dimethylcyclopropane carboxylate (compound No. 11, Table I) consisting of 50% w/w of the (±)-cis isomer and 50% w/w of the (±)-trans isomer.

The compounds of formula I may be used to combat and control infestations of insect pests and also other invertebrate pests, for example, acarine pests. The insect and acarine pests which may be combatted and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise a insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10-85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:

*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back month, larvae)
*Phaedon cochleariae* (mustard beetle)
*Telarius cinnabarinus* (carmine spider mite)
Aonidiella spp. (scale insects)
Trialeuroides spp. (white flies)
*Blattella germanica* (cockroaches)
*Spodoptera littoralis* (cotton leaf worm)
*Chortiocetes terminifera* (locusts)
Diabrotica spp. (rootworms)

The compounds of formula I and compositions comprising them have shown themselves to be particularly useful in controlling lepidopteran pests of cotton, for example Spodoptera spp. and Heliothis spp. The fumigant properties of the compounds enable them to be used to combat pests which inhabit the soil, for example Diabrotica spp. They are also excellent knock down agents and as such may be used in conjunction with other insecticides to combat public health pests such as flies. They are also very useful in combatting insect and acarine pests which infest domestic animals, such as *Lucilia sericata*, and ixodid ticks such as Boophilus spp., Ixodes spp., Amblyomma spp., Rhipicephalus spp., and Dermaceutor spp. They are effective in combatting both susceptible and resistant strains of these pests in their adult, larval and intermediate stages of growth, and may be applied to the infested host animal by topical, oral or parenteral administration.

The following Examples illustrate the various aspects of the invention.

EXAMPLE 1

This Example illustrates the insecticial properties of the Products A to L.

The activity of the products was determined using a variety of insect pests. The product was used in the form of liquid preparations containing 1000, 500, 50 or 25 p.p.m. by weight of the product. The preparations were made by dissolving the product in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the product. "Lissapol" is a Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment. Details are given in Table IIA.

The results of the tests are given in Table IIB for each of the products A to Z at the rate in parts per million given in the second column as a grading of mortality on a scale of 0-9 wherein

| 0 | represents | less than 10% | mortality |
|---|---|---|---|
| 1 | represents | from 10 to 19% | mortality |
| 2 | represents | from 20 to 29% | mortality |
| 3 | represents | from 30 to 39% | mortality |
| 4 | represents | from 40 to 49% | mortality |
| 5 | represents | from 50 to 59% | mortality |
| 6 | represents | from 60 to 69% | mortality |
| 7 | represents | from 70 to 79% | mortality |
| 8 | represents | from 80 to 89% | mortality |
| 9 | represents | from 90 to 100% | mortality |

In Table IIB the pest organism used is designated by a letter code and the pest species, the support medium or food, and the type and duration of test is given in Table IIA.

TABLE IIA

| CODE LETTERS (Table IIB) | PEST SPECIES | SUPPORT MEDIUM/FOOD | TYPE OF TEST* | DURATION (days) |
|---|---|---|---|---|
| MD | *Musca domestica* (houseflies - adults) | Cotton wool/ milk, sugar | Contact | 2 |
| SL | *Spodoptera littoralis* (cotton leaf worm - larvae) | Cotton leaves | Residual | 1 |
| PX | *Plutella xylostella* (diamond back moth - larvae) | Mustard leaves | Residual | 3 |
| SG | *Sitophilus granarius* (grain weevil - adults) | Grain | Contact | 3 |
| DB | *Diabrotica balteata* (rootworm - larvae) | Filter paper | Contact | 3 |

*"Contact" test indicates that both pests and medium were treated and "residual" indicates that the medium was treated before infestation with the pests.

TABLE IIB

| PRODUCT | RATE (ppm) | MD | SL | PX | SG | DB |
|---|---|---|---|---|---|---|
| A | 500 | 6 | 7 | 9 | 9 | 9 |
| B | 50(25) | 9 | 4 | 0 | 0 | (9) |
| C | 500 | 8 | 3 | 0 | 0 | 0 |
| D | 50 | 9 | 9 | 9 | 9 | 9 |
| E | 500 | 9 | 9 | 6 | 0 | 0 |
| F | 25 | 9 | 9 | 9 | 9 | 9 |
| G | 50 | 9 | 0 | 4 | 0 | 2 |
| H | 1000 | 9 | 9 | 9 | 9 | 9 |
| J | 1000 | 9 | 9 | 9 | — | 9 |
| K | 1000 | 9 | 9 | 9 | — | 9 |
| L | 50 | 9 | 9 | 7 | 7 | — |

In further tests the products showed insecticidal activity against a number of other species. Thus for example Products A,C,H,J and K showed activity against red spider mite adults (*Tetranychus telarius*) and Products A, F, G, J and K showed good aphicidal properties against *Aphis fabae*.

EXAMPLE 2

This Example illustrates the preparation of 2,3,5,6-tetrafluoro-4-toluic acid.

(a) Preparation of 2,3,5,6-tetrafluorotoluene

A solution of n-butyllithium in hexane (1.6 M, 62.5 ml) was added dropwise to a well stirred solution of 1,2,4,5-tetrafluorobenzene (15.0 g) in dry tetrahydrofuran (150 ml) maintained at a temperature of −60° C. under an atmosphere of dry argon. When the addition was complete the mixture was stirred at −45° C. for 2 hours and then methyl iodide (14.2 g) was added dropwise whilst the temperature was kept at −45° C. After a period of 30 minutes the mixture was allowed to warm to the ambient temperature, poured into distilled water and the mixture extracted with diethyl ether (2×50 ml), and the extracts dried over anhydrous magnesium sulphate. After filtering the solution was concentrated by evaporation of the solvents at atmospheric pressure. The residual oil was distilled and the fraction boiling in the range 115°–122° C. at atmospheric pressure (6.2 g) collected, identified by n.m.r. and gas chromatographic analysis as consisting of ca. 95% of the required 2,3,5,6-tetrafluorotoluene and ca. 5% of 2,3,5,6-tetrafluoro-1,4-xylene.

(b) Preparation of 2,3,5,6-tetrafluoro-4-toluic acid

The product of step (a) above (4.3 g) was mixed with diethyl ether (30 ml), the mixture cooled to −70° C., and maintained at this temperature whilst a solution of n-butyllithium in n-hexane (1.6 M, 16.4 ml) was slowly added. The mixture was stirred for a period of 1 hour during which time a fine white precipitate was formed. Dry carbon dioxide gas was then passed into the mixture for 30 minutes whilst the temperature was maintained within the range −70° to −40° C., and continued to be passed in thereafter whilst the mixture was allowed to warm to the ambient temperature. After acidifying with dilute hydrochloric acid (6 N, 40 ml) the organic phase was separated, washed with water and dried over anhydrous magnesium sulphate. After evaporation of the solvents under reduced pressure the residual solid was recrystallised from toluene to yield 2,3,5,6-tetrafluoro-4-toluic acid, m.p. 170° C. identified by infra red and nuclear magnetic resonance spectroscopy.

EXAMPLE 3

This Example illustrates the preparation of 4-methoxycarbonyl-2,3,5,6-tetrafluorotoluene.

A mixture of 2,3,5,6-tetrafluoro-4-toluic acid (1.0 g), methanol (5.0 ml) and concentrated sulphuric acid (0.25 ml) was heated at the reflux temperature for 10 hours, cooled and poured into an ice/water mixture. The resultant mixture was extracted with diethyl ether, the extract washed with water, dried over anhydrous magnesium sulphate and concentrated by evaporation of the solvent. The residual oil was identified by infra red spectroscopy as 4-methoxycarbonyl-2,3,5,6-tetrafluorotoluene.

Infra red: 1740 cm$^{-1}$.

EXAMPLE 4

This Example illustrates the preparation of 4-cyano-2,3,5,6-tetrafluorotoluene.

(a) Preparation of 2,3,5,6-tetrafluoro-4-toluamide

A mixture of 2,3,5,6-tetrafluoro-4-toluic acid (1.0 g) and thionyl chloride (4.0 ml) was heated at the reflux temperature for 4 hours, cooled, and the excess thionyl chloride removed by azeotropic distillation with toluene. The residual acid chloride was added dropwise to a vigorously stirred solution of ammonia (s.g=0.880, 5 ml) at 5° C. When the addition was complete the mixture was stirred for 30 minutes, and the solid precipitate collected by filtration, washed with water and dried, to yield 2,3,5,6-tetrafluoro-4-toluamide, m.p. 157°–158° C. (toluene).

(b) Preparation of 4-cyano-2,3,5,6-tetrafluorotoluene

A solution of phosphorus oxychloride (1.4 g) in methylene chloride (4 ml) was added slowly to a solution of 2,3,5,6-tetrafluoro-4-toluamide (1.0 g) in pyridine (8 ml) at $-5°$ C. When the addition was complete the mixture was warmed to the ambient temperature over a period of 90 minutes, poured into a mixture of dilute hydrochloric acid and ice, and the resultant mixture was extracted with methylene chloride. After washing the extract with water (three times) and drying over anhydrous magnesium sulphate, the solvent was removed by evaporation under reduced pressure. The residual oil was purified by distillation under water pump pressure in a Kugelrohr apparatus to yield 4-cyano-2,3,5,6-tetrafluorotoluene, identified by infra red spectroscopy.

EXAMPLE 5

This Example illustrates the preparation of 4-methylcarbonyl-2,3,5,6-tetrafluorotoluene.

The acid chloride obtained from 2,3,5,6-tetrafluoro-4-toluic acid (1.0 g) as described in Example 4 was dissolved in diethyl ether (25 ml) and the solution cooled to $-70°$ C.

A solution of methyl lithium in diethyl ether (concentration 1.4 M, 3.5 ml) was slowly added to the solution of acid chloride, the resultant mixture stirred for one hour at $-70°$ C., and then allowed to warm to the ambient temperature and poured into water. The resultant mixture was extracted with diethyl ether, and the extracts washed with water and dried over anhydrous magnesium sulphate. After removal of the solvents the residual oil was purified by column chromatography using a silica gel column and chloroform eluent, and by distillation under water pump pressure in a Kugelrohr apparatus, to give 4-methylcarbonyl-2,3,5,6-tetrafluorotoluene, identified by infra red spectroscopy.

EXAMPLE 6

This Example illustrates the preparation of 4-trifluoromethyl-2,3,5,6-tetrafluorotoluene.

A solution of methyl lithium in diethyl ether (concentration 1.4 M, 91.0 ml) was added to a stirred solution of octafluorotoluene (30.0 g) in diethyl ether (100 ml) under a dry argon atmosphere at a rate just sufficient to maintain the temperature of the mixture at the reflux point. After the addition had been completed the mixture was heated at the reflux temperature for a further three hours. After cooling to the ambient temperature the mixture was poured into water, and the resultant mixture extracted with diethyl ether, the extracts dried over anhydrous magnesium sulphate, and concentrated by evaporation of the ether at atmospheric pressure. The residual liquid was distilled at atmospheric pressure and the fraction boiling at 128°–129° C. Examination by infra red and $^{19}$F n.m.r. spectroscopy showed it to be the required 4-trifluoromethyl-2,3,5,6-tetrafluorotoluene.

EXAMPLE 7

This Example illustrates the preparation of 4-trifluoromethyl-2,3,5,6-tetrafluorobenzyl bromide.

A mixture of 4-trifluoromethyl-2,3,5,6-tetrafluorotoluene (16.0 g), N-bromosuccinimide (15.0 g), dry carbon tetrachloride (80 ml) and benzoyl peroxide (0.5 g), was heated at the reflux temperature for 20 hours. After removal of the solid residue by filtration the filtrate was diluted with diethyl ether, washed with water, dried over anhydrous magnesium sulphate and concentrated by evaporation of the solvents under reduced pressure. The residual oil was distilled under reduced pressure and the fraction boiling over the range 104°–108° C. at 45 mm Hg. collected and identified by n.m.r. and infra red spectroscopy as 4-trifluoromethyl-2,3,5,6-tetrafluorobenzyl bromide.

Infra red: 1656, 1495, 1330, 1148, 985 cm$^{-1}$.

EXAMPLE 8

By the procedure of Example 7 the following benzyl bromides were prepared from the corresponding toluenes.

4-cyano-2,3,5,6-tetrafluorobenzyl bromide from 4-cyano-2,3,5,6-tetrafluorotoluene.

N.m.r. ($^1$H(ppm)CDCl$_3$): 4.46–4.56 (2s, 2H).

Infra red: 2240, 1685, 1650, 1490 cm$^{-1}$.

4-methoxycarbonyl-2,3,5,6-tetrafluorobenzyl bromide from 4-methoxycarbonyl-2,3,5,6-tetrafluorotoluene.

N.m.r. ($^1$H(ppm)CDCl$_3$): 4.00 (s,3H); 4.50–4.58 (2s,2H). Infra red: 1740, 1654, 1485 cm$^{-1}$.

4-methylcarbonyl-2,3,5,6-tetrafluorobenzyl bromide from 4-methylcarbonyl-2,3,5,6-tetrafluorotoluene.

N.m.r. ($^1$H(ppm)CDCl$_3$): 2.62 (s,3H); 4.46–4.56 (2s,2H).

EXAMPLE 9

This Example illustrates the preparation of 2-nitro-4-fluorobenzyl bromide.

A mixture of 2-nitro-4-fluorotoluene (1.65 g), N-bromo-succinimide (1.78 g), carbon tetrachloride 10.0 ml) and benzoyl peroxide (0.1 g) was heated at the reflux temperature until the solid residue was observed to be floating at the surface (ca. 3 hours). After removing the solid by filtration, the filtrate was diluted with diethyl ether, washed with water, dried over anhydrous magnesium sulphate and concentrated by evaporation of the solvents under reduced pressure. The residue (estimated to contain ca. 35% w/w of the benzyl bromide in admixture with unchanged starting material) was subjected to column chromatography using a silica column and diethyl ether/petroleum ether (ratio 1:9 v/v) as eluent to yield pure 2-nitro-4-fluorobenzyl bromide.

EXAMPLE 10

By the use of the procedure set out in Example 9 the following benzyl bromides were obtained from the corresponding toluenes.

3-Fluoro-4-nitrobenzyl bromide from 3-fluoro-4-nitrotoluene.

2-Fluoro-4-nitrobenzyl bromide from 2-fluoro-4-nitrotoluene.

2-Fluoro-5-nitrobenzyl bromide from 2-fluoro-5-nitrotoluene.

EXAMPLE 11

This Example illustrates the preparation of 4-trifluoromethylbenzyl 3-(2-chloro-3,3,3-trifluoroprop-1-en-1-yl)-2,2-dimethylcyclopropane carboxylate (compound no. 11, Table I) consisting of 50% w/w of the ($\pm$)-cis isomer and 50% w/w of the ($\pm$)-trans isomer (Product L).

A mixture of thionyl chloride (3.0 ml) and 3-(2-chloro-3,3,3-trifluoroprop-1-en-1-yl)-2,2-dimethylcyclopropane carboxylic acid (50% cis, 50% trans, (w/w), 0.500 g) was heated at the reflux temperature for 5 hours, and then kept at the ambient temperature for 16 hours. After removing the excess thionyl chloride by evaporation under reduced pressure (the last traces being removed by azeotropic distillation with toluene) the resultant acid chloride was added to a mixture of 4-trifluoromethylbenzyl alcohol (0.363 g), dry pyridine (0.163 g) and dry toluene (10 ml), and the resultant mixture stirred at the ambient temperature for 2 hours and then stood at the ambient temperature for a further 16 hours. After adding toluene (10 ml) the mixture was washed successively with dilute hydrochloric acid (2 N, 20 ml), water and saturated sodium bicarbonate solution, dried over anhydrous magnesium sulphate and concentrated by evaporation of the solvent under reduced pressure yielding, as a residual oil, 4-trifluoromethylbenzyl 3-(2-chloro-3,3,3-trifluoroprop-1-en-1-yl)-2,2-dimethylcyclopropane carboxylate, identified by n.m.r. and infra red spectroscopy.

N.m.r. ($^1$H(ppm)CDCl$_3$): 1.24–1.44(m,6H); 1.80–2.60(m,2H); 5.22–5.28(2s,2H); 6.22,7.02(2d,1H); 7.50–7.80(m,4H).

EXAMPLE 12

By the use of the procedure set out in Example 11 above the following products were prepared from the stated acids and alcohols, and identified by their n.m.r. and infra red spectra.

Product A from 2-trifluoromethylbenzyl alcohol and 3-(2-chloro-3,3,3-trifluoroprop-1-en-1-yl)-2,2-dimethylcyclopropane carboxylic acid (50% cis, 50% trans, w/w). N.m.r. ($^1$H(ppm)CDCl$_3$): 1.24–1.44(m,6H); 1.80–2.60 (m,2H); 5.38–5.44(2s,2H); 6.24,7.02 (2d,1H); 7.44–7.84 (m,4H).

Product B from 3-trifluoromethylbenzyl alcohol and 3-(2-chloro-3,3,3-trifluoroprop-1-en-1-yl)-2,2-dimethylcyclopropane carboxylic acid (50% cis, 50% trans, w/w).

EXAMPLE 13

This Example illustrates the preparation of 4-trifluoromethyl-2,3,5,6-tetrafluorobenzyl 3-(2-chloro-3,3,3-trifluoroprop-1-en-1-yl)-2,2-dimethylcyclopropane carboxylic acid (compound no. 4, Table I) consisting of 50% w/w of the ($\pm$)-cis isomer and 50% w/w of the ($\pm$)-trans isomer. (Product D).

3-(2-Chloro-3,3,3-trifluoroprop-1-en-1-yl)-2,2-dimethylcyclopropane carboxylic acid (50% cis, 50% trans, w/w, 1.0 g) was added to a mixture of 4-trifluoromethyl-2,3,5,6-tetrafluorobenzyl bromide (1.25 g), anhydrous potassium carbonate (0.55 g) and dry acetone (10 ml) at the ambient temperature, and the mixture stirred at the ambient temperature for two hours. Dilute hydrochloric acid (2 N,10 ml) was added and the resultant mixture extracted with chloroform, the extracts washed with water, dried over anhydrous magnesium sulphate and the volatile portion removed by evaporation under reduced pressure. The residual oil was shown by n.m.r. and infra red spectroscopy to be 4-trifluoromethyl-2,3,5,6-tetrafluorobenzyl 3-(2-chloro-3,3,3-trifluoroprop-1-en-1-yl)-2,2-dimethylcyclopropane carboxylate.

N.m.r. ($^1$H(ppm)CDCl$_3$): 1.24–1.44(m,6H); 1.74–2.52 (m,2H); 5.28–5.40 (2s,2H); 6.22,6.96(2d,1H).

EXAMPLE 14

By the use of the procedure set out in Example 13 the following products were obtained from the stated acids and benzyl bromides, and identified by their n.m.r. and infra red spectra.

Product F from 4-trifluoromethyl-2,3,5,6-tetrafluorobenzyl bromide and 3-(2,2-dichlorovinyl)-2,2-dimethylcyclopropane carboxylic acid (50% cis, 50% trans, w/w).

N.m.r. ($^1$H(ppm)CDCl$_3$): 1.20–1.42(m,6H); 1.60–2.40 (m,2H); 5.30–5.40 (2s,2H); 5.70,6.32 (2d,1H).

Product H from 4-methoxycarbonyl-2,3,5,6-tetrafluorobenzyl bromide and 3-(2-chloro-3,3,3-trifluoroprop-1-en-1-yl)-2,2-dimethylcyclopropane carboxylic acid (50% cis, 50% trans, w/w).

N.m.r. ($^1$H(ppm)CDCl$_3$): 1.24–1.44(m,6H); 1.70–2.52 (m,2H); 4.06 (s,3H); 5.26–5.36 (2s,2H); 6.22,6.94 (2d,1H).

Product J from 4-methylcarbonyl-2,3,5,6-tetrafluorobenzyl bromide and 3-(2-chloro-3,3,3-trifluoroprop-1-en-1-yl)-2,2-dimethylcyclopropane carboxylic acid (50% cis, 50% trans, w/w).

N.m.r. ($^1$H(ppm)CDCl$_3$): 1.24–1.44(m,6H); 1.70–2.52 (m,2H); 2.60(t,3H); 5.22–5.30 (2s,2H); 6.12,6.82(2d,1H).

Product K from 4-cyano-2,3,5,6-tetrafluorobenzyl bromide and 3-(2-chloro-3,3,3-trifluoroprop-1-en-1-yl)-2,2-dimethylcyclopropane carboxylic acid (50% cis, 50% trans, w/w).

N.m.r. ($^1$H(ppm)CDCl$_3$): 1.24–1.44 (m,6H); 1.74–2.50 (m,2H); 5.24–5.32(2s,2H); 6.08,6.78(2d,1H).

EXAMPLE 15

The procedure of Example 13 was used (except that the mixture was stirred at the ambient temperature for 8 hours and after filtration to remove inorganic material the acetone solution was evaporated to yield the product without acid treatment or washing) to prepare the following products.

Product E from 3-fluoro-4-nitrobenzyl bromide and 3-(2-chloro-3,3,3,-trifluoroprop-1-en-1-yl)-2,2-dimethylcyclopropane carboxylic acid (50% cis, 50% trans, w/w).

N.m.r ($^1$H(ppm)CDCl$_3$): 1.24–1.38 (m,6H); 1.60–2.60 (m,2H); 5.20 (2s,2H); 6.22–6.90(2d,1H); 7.18–8.18(m,3H).

Product C from 2-nitro-4-fluorobenzyl bromide and 3-(2-chloro-3,3,3-trifluoroprop-1-en-1-yl)-2,2-dimethylcyclopropane carboxylic acid (50% cis, 50% trans, w/w).

Product G from 2-fluoro-4-nitrobenzyl bromide and 3-(2-chloro-3,3,3-trifluoroprop-1-en-1-yl)-2,2-dimethylcyclopropane carboxylic acid 50% cis, 50% trans, w/w).

We claim:

1. A compound of the formula

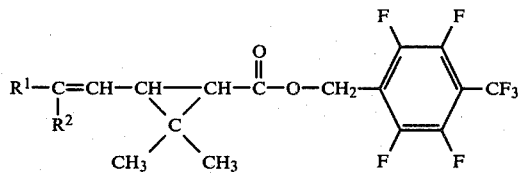

wherein $R^1$ and $R^2$ are both chloro or one of $R^1$ and $R^2$ is chloro and the other is trifluoromethyl.

2. A method of combating insects at a locus which comprises treating the locus with an insecticidally effective amount of a compound of claim 1.

* * * * *